US010004778B1

(12) United States Patent
Hasson et al.

(10) Patent No.: US 10,004,778 B1
(45) Date of Patent: Jun. 26, 2018

(54) METHOD OF MAKING AN AJWA DATE-BASED TREATMENT FOR SNAKE ENVENOMATION

(71) Applicant: SULTAN QABOOS UNIVERSITY, Muscat (OM)

(72) Inventors: Sidgi S. A. A. Hasson, Muscat (OM); Ali A. H. Al Jabri, Muscat (OM)

(73) Assignee: SULTAN QABOOS UNIVERSITY, Muscat (OM)

( * ) Notice: Subject to any disclaimer, the term of this patent is extended or adjusted under 35 U.S.C. 154(b) by 37 days.

(21) Appl. No.: 15/605,923

(22) Filed: May 25, 2017

(51) Int. Cl.
A61K 36/889 (2006.01)
A61K 9/00 (2006.01)
A61K 9/19 (2006.01)

(52) U.S. Cl.
CPC ......... *A61K 36/889* (2013.01); *A61K 9/0019* (2013.01); *A61K 9/19* (2013.01); *A61K 2236/15* (2013.01); *A61K 2236/33* (2013.01)

(58) Field of Classification Search
None
See application file for complete search history.

(56) References Cited

U.S. PATENT DOCUMENTS 8,852,651 B1 10/2014 Al-Shehry
2016/0136226 A1 5/2016 Alghamdi

FOREIGN PATENT DOCUMENTS

WO WO 2013/012302 A2 1/2013

OTHER PUBLICATIONS

Khan, F., Ahmed, F., Pushparaj, P.N., Abuzenadah, A., Kumosani, T., Barbour, E., et al., Ajwa Date (*Phoenix dactylifera* L.) Extract Inhibits Human Breast Adenocarcinoma (MCF7) Cells In Vitro by Inducing Apoptosis and Cell Cycle Arrest, Plos ONE, 11(7), 1-17. (Year: 2016).*
Saleh et al. "Phenolic Contents and Antioxidant Activity of Various Date Palm (*Phoenix dactylifera* L.) Fruits from Saudi Arabia". Food and Nutrition Sciences, 2, 1134-1141 (especially p. 1135). (Year: 2011).*
Kerton, F.M. Chapter 5 from "Alternative Solvents for Green Chemistry". Royal Society of Chemistry, p. 102. (Year: 2009).*
"Recrystallization". Internet archive date: Sep. 19, 2003 [Retrieved from the Internet on: Sep. 26, 2017]. Retrieved from: <URL: https://web.archive.org/web/20030919013759/http://www.pitt.edu/~bandik/organicweb/recrystallization.html>. (Year: 2003).*
(U1) "Hypertonic Saline". Internet Archive date: 2008—[Retrieved from the Internet on: Sep. 26, 2017]. Retrieved from: <URL: https://web.archive.org/web/20081024043122/http://www.rxlist.com/hypertonic-saline-drug.htm>. (Year: 2008).*
Vyawahare, N., et al. "*Phoenix dactylifera*: An update of its indegenous uses, phytochemistry and pharmacology." *Internet J Pharmacol* 7.1 (2009): 1-11.
Bashandy et al., "Protective effects of date palm extract as natural antioxidants on hepatotoxicity induced by *Cerastes cerastes* venom in albino rats." *International Journal of Advanced Research* (2016), vol. 4, Issue 3, 647-665.

* cited by examiner

*Primary Examiner* — Amy L Clark
(74) *Attorney, Agent, or Firm* — Richard C. Litman

(57) ABSTRACT

The method of making an Ajwa date-based treatment for snake envenomation is a method for preparing a composition for the treatment of local hemorrhage and edema induced by snake envenomation. The composition is an ethanolic extract of the fruit of the Ajwa date palm (*Phoenix dactylifera* L.). A concentrated, granulated extract of the Ajwa date is produced by repeated suspension in ethanol, extraction, filtering, and drying the filtrate to evaporate the solvent. The final filtrate is lyophilized (i.e., freeze-dried) to yield a granulated Ajwa date-based treatment for snake envenomation. This granulated Ajwa date-based treatment for snake envenomation may then be further suspended in a saline solution for preparation of an intravenous treatment for snake envenomation.

2 Claims, 1 Drawing Sheet

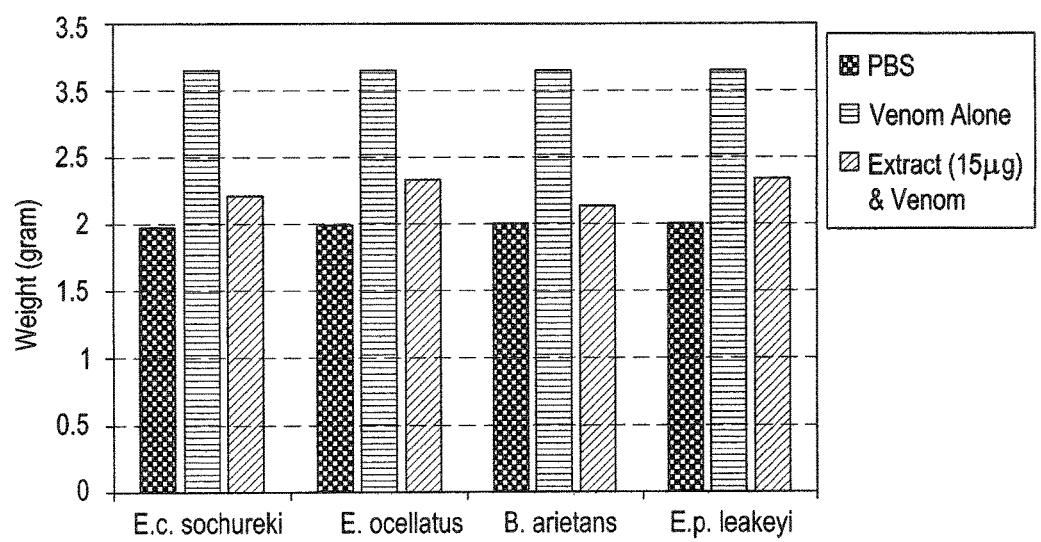

METHOD OF MAKING AN AJWA DATE-BASED TREATMENT FOR SNAKE ENVENOMATION

BACKGROUND OF THE INVENTION

1. Field of the Invention

The present invention relates to treatments for snake envenomation, and particularly to a method of making an Ajwa date-based composition for treatment for snake envenomation that uses an ethanolic extract of date fruits from the Ajwa date palm (*Phoenix dactylifera* L.) to treat local hemorrhage and edema induced by snake bite from venomous snakes.

2. Description of the Related Art

Snake venom is highly modified saliva containing zootoxins that facilitate the immobilization and digestion of prey, and also defend against threats. The venom is injected by unique fangs after a bite, although some species of snake are also able to spit the venom. Venoms contain more than 20 different compounds, mostly in the form of proteins and polypeptides. A complex mixture of proteins, enzymes and various other substances (with toxic and lethal properties) serve to immobilize and digest prey.

Snake toxins vary greatly in their functions. Two broad classes of toxins found in snake venoms are neurotoxins (mostly found in elapids) and hemotoxins (mostly found in viperids). Neurotoxic venom acts on the nervous system and brain, and hemotoxic venoms act on the heart and cardiovascular system. Examples of the latter include bites from the boomslang snake (*Dispholidus typus*) and the twig snake (*Thelotornis* spp.). The venom of these snakes is toxic to blood cells and thins the blood (i.e., hemotoxic and hemorrhagic effects). Early symptoms include headaches, nausea, diarrhea, lethargy, mental disorientation, bruising and bleeding at the site of the bite as well as all body openings. Exsanguination is the main cause of death from such a bite. In addition to nausea, internal bleeding and exsanguination, one can die from a brain hemorrhage and/or respiratory collapse.

In addition to the above, proteolytic venom dismantles the molecular structure of the area surrounding and including the bite, and cytotoxic venom has a localized action at the site of the bite. Each of these types of venom can cause a wide variety of serious conditions, including edema and necrosis of the envenomed tissue. Although great efforts have been dedicated to effect remedial and preventive methods of envenomation, there is currently no adequate treatment for local hemorrhage, edema or necrosis. Intravenous administration of antivenin, prepared from IgG of venom-immunized horses or sheep, is an effective treatment for systemic envenoming. However, antivenin has only limited effectiveness against the effects of local hemorrhage and edema that develop rapidly after snakebite.

Thus, a method of making an Ajwa date-based treatment for snake envenomation solving the aforementioned problems is desired.

SUMMARY OF THE INVENTION

The method of making an Ajwa date-based treatment for snake envenomation is a method for preparing a composition for the treatment of local hemorrhage and edema induced by snake envenomation. The composition is an ethanolic extract of the fruit of the Ajwa date palm (*Phoenix dactylifera* L.). The fruit from an Ajwa date palm (i.e., an Ajwa date) is initially dried, preferably in sunlight, until the inside of the fruit becomes black. The fruit is then sliced and ground. The ground and dried fruit is mixed with 96% ethanol to form an Ajwa date suspension. The suspension is incubated at room temperature for 72 hours under continuous vigorous shaking. Following this period, the Ajwa suspension is filtered to separate out a filtrate from the herbal solution. The filtrate is dried at a temperature of 45° C. or until it becomes viscous, evaporating the solvent to obtain a crude extract.

The crude extract is suspended in 96% ethanol and incubated at 75° C. overnight, followed by cooling on ice so that a solid forms in the solution. The solid is removed by filtration, and the filtrate is lyophilized (i.e., freeze-dried) to yield a granulated Ajwa date-based treatment for snake envenomation. This granulated Ajwa date-based treatment for snake envenomation may then be further suspended in a saline solution for preparation of an intravenous treatment.

These and other features of the present invention will become readily apparent upon further review of the following specification and drawings.

BRIEF DESCRIPTION OF THE DRAWINGS

The sole drawing FIGURE is a chart showing the response of test animals to edema induced by the venom of various snakes, particularly comparing a control group with no treatment, a control group which received phosphate buffered saline (PBS), and group which received a treatment made by the method of making an Ajwa date-based treatment for snake envenomation according to the present invention.

DETAILED DESCRIPTION OF THE PREFERRED EMBODIMENTS

The method of making an Ajwa date-based treatment for snake envenomation is a method for preparing a composition for the treatment of local hemorrhage and edema induced by snake envenomation. The composition is an ethanolic extract of the fruit of the Ajwa date palm (*Phoenix dactylifera* L.) (i.e., an Ajwa date). The fruit from an Ajwa date palm is initially dried, preferably in sunlight, until the inside of the fruit becomes black. The fruit is then sliced and ground. The ground and dried fruit is mixed with 96% ethanol to form an Ajwa date suspension. The suspension is incubated at room temperature for 72 hours under continuous vigorous shaking. Following this period, the Ajwa suspension is filtered to separate out a filtrate from the herbal solution. The filtrate is dried at a temperature of 45° C. or until it becomes viscous, evaporating the solvent to obtain a crude extract.

The crude extract is suspended in 96% ethanol and incubated overnight at a temperature of 75° C. on a conventional heat block or the like, followed by cooling on ice so that a solid forms in the solution. The solid is removed by filtration, and the filtrate is lyophilized (i.e., freeze-dried) to yield a granulated Ajwa date-based treatment for snake envenomation. This granulated Ajwa date-based treatment for snake envenomation may then be further suspended in a saline solution for preparation of an intravenous treatment.

In experiments that are described in greater detail below, the intravenous treatment noted above was prepared by re-suspending the lyophilized granules in physiological saline solution, which was sterilized using a 0.45 μm microring syringe filter and kept in sterile Eppendorf tubes at −20° C. The sterile medicament herbal extract was incubated at 37° C. for 10 to 15 minutes prior to injection. Each injection was adjusted to 0.5 g per kg weight (unless otherwise stated in the description of the experiments below).

It should be understood that the granulated Ajwa date-based treatment for snake envenomation may be further processed and formulated in a form suitable to be administered orally, or alternatively, may be parenterally administrated as an injection or infusion, e.g., through intravenous, subcutaneous or intramuscular injection.

In order to examine potential toxicity of the Ajwa date-based treatment during oral administration in animals, both rabbits (Group A) and WKY rats (Group B) were used for conducting a standard toxicity profile. Included in Group A were a total of 15 rabbits, including 10 males and 5 females, each weighing between 800 g and 1300 g. Group B included a total of 15 WKY rats, with 9 males and 6 females, each weighing between 300 g and 600 g. Both groups were randomly divided to investigate lethal dosage. The Ajwa date-based treatment was administered orally by intubation at variable dosages to reach an optimum of 16 g/kg for each animal group. The concentration of each fluid dosage containing the herbal composition was about 1 g/ml. The higher dosage group (15 g/kg) had a volume of about 15 ml. The extract was given to the animals on a daily basis for two weeks.

The animals' behavior was observed continuously for a period of two weeks after administration. Observation was conducted hourly on the first day, and during the following days, observation was conducted four to six times per day. At the end of the observation period, the animals were sacrificed and dissected to examine the eyes, liver, lung and spleen for adverse effects. Similar experiments were performed with 1-2 g/kg administered intravenously.

The results of the oral and intravenous administration of the herbal extract showed no abnormality in the behavior of either group of mammals, both during and after the observation period. All animals were alive after two weeks of administration of the presumed lethal dosage of 16 g/kg (orally) and 2 g/kg (intravenously). During the observation period, the body weight of the rabbits and rats, administered either with the oral or intravenous dose of 16 g/kg or 2 g/kg, respectively, increased significantly in a pattern similar to that of the control animals, indicating that the animals continued to mature without any significant toxic effects. Biochemical analysis showed normal ranges of ALT, AST, CBC and GGT. Inspection of the eyes, liver, lung and spleen (after scarification and dissection) showed no extraordinary signs. The results, when compared to a general acute toxicity index, were normal, and no acute toxicity was observed. From this, the weight ratio of diffuse Ajwa date extract is determined to be 1-15 g/kg orally and 2 g/kg intravenously.

In a further preclinical trial performed on rats, mice and rabbits envenomed by different species of snakes, the Ajwa date extract treatment, adjusted to 1.5 g/kg (5 mL), was administered orally three times a day (every eight hours) over the course of one week. The treatment was delivered before feeding for maximum absorption rates. None of the animals were treated with any other medication or pharmaceutical preparation. Prior to treatment, a physical examination of each subject indicated common symptoms of envenomation, including weakness, depression, edema, stegnosis, loss of appetite, weight loss and necrosis.

An additional trial was performed with administration of both snake venom and the Ajwa date extract after pre-incubation. Thirty-two adult WKY rats of both genders (250-360 g) were divided into two groups. Group 1 was divided into four equal subgroups of four WKY rats. Group 1 was injected subcutaneously with *E.c. sochureki* (75 µg/kg), *Echis ocellatus* (50 µg/kg), *Bitis arietans* (60 µg/kg) or *Echis pyramidum leakeyi* (75 µg/kg) venoms alone, where the dose was previously determined to induce 10±2 mm acute skin hemorrhage. Group 2 was also divided into four equal subgroups of four WKY rats. Group 2 was injected subcutaneously with a mixture of either *E. c. sochureki, Echis ocellatus, Bitis arietans* or *Echis pyramidum leakeyi* venom and 1.5 mg/kg of the Ajwa ethanolic extract after both venom and extract were incubated in an Eppendorf tube at 37° C. for 30 minutes. All animals were observed over a period of 24 hours. At the end of the observation period, the animals were sacrificed, and their skins were dissected to examine the hemorrhage neutralization efficacy of the Ajwa date extract. With regard to inhibition of venom-induced local hemorrhage, Group 1 showed 10±2 mm acute skin hemorrhage, whereas Group 2 showed no signs of acute skin hemorrhage ($P<0.002$).

A similar procedure was carried out with 64 WKY rats, except that the animals were injected with the Ajwa date extract intramuscularly (IM) one to five minutes after venom injection at the site where the venom was injected. In this experiment, two controls were used, including South African Institute for Medical Research (SAIMR) *echis* antivenin 100 µL, (1 µg/mL), and Costus 1.5 mg/kg as a placebo. Group 1 showed 10±2 mm acute skin hemorrhage. Groups 2 and 3 (16 rats each) included WKY rats treated with independent injections of the Costus (1.5 mg/kg) or SAIMR to the venom-injected site, respectively, and also showed signs of acute skin hemorrhage. In contrast, Group 4 included the 16 WKY rats treated with independent injection of the Ajwa date extract (1.5 mg/kg). Group 4 showed complete neutralization of the venom-induced hemorrhage ($P<0.005$).

Oral administration of the Ajwa date extract was also tested 30 minutes after venom injection. Thirty-two adult CD1 Swiss mice of both genders (25-35 g) were divided into two groups. Group 1 was divided into four equal subgroups of four CD1 Swiss mice. Group 1 was injected subcutaneously with *E.c. sochureki* (75 µg/kg), *Echis ocellatus* (50 µg/kg), *Bitis arietans* (60 µg/kg) or *Echis pyramidum leakeyi* (75 µg/kg) venom alone. Group 2 was also divided into four equal subgroups (Group 2.1 to Group 2.4) of four CD1 Swiss mice each. All of the subgroups were injected with the venom subcutaneously with the same dose of each venom stated above 30 minutes prior to oral administration of the Ajwa date extract by gastric intubation. The Ajwa date extract was administered at a dosage of 1.5 g, three times in the first day and twice a day for the subsequent two days. 16 animals at each interval were sacrificed and their skins were dissected to examine the neutralization efficacy of the Ajwa date extract after 16 and 32 hours, respectively. After 32 hours, the Ajwa date extracts showed significant neutralization efficacy when compared with the results after 16 hours. This indicates that oral administration takes time for effectiveness, particularly in contrast to the results of direct IM injection to the site of envenomation.

Edema-inducing activity was assayed by dividing Group 1 into four equal subgroups (of 10 WKY rats for each venom species given directly above), followed by injection in the right footpad with three times the minimum edema dose (MED) (7.5 µg for all venoms) of venom sample (dissolved in 20 µL PBS, pH 7.2). The left footpads received saline as a control. The legs were cut off at the ankle joint after six hours. An increase in weight due to edema was calculated as the edema ratio, which equals the weight of the edematous leg times 100/weight of control leg. The MED was defined as the amount of venom sample required to cause an edema of 100%. Group 2 (for inhibition examination) was divided into four equal subgroups (10 WKY rats in each), and each subgroup was injected subcutaneously with the venom sample that was preincubated with the extract at 15 μg concentrations for 30 minutes at 37° C. The results were statistically analyzed using ANOVA and the student's t-test. The minimum dose for hemorrhage (MHD) was found to be 7.5 μg (i.e., the amount of venom sample required to cause an edema of 100%). Three times the MHD was found to cause an edema of 160+2.0%. The venom-induced hemorrhagic edema was also inhibited by the Ajwa date extract. At a ratio of venom to extract of 1:60 and 1:70 (w/w), the edema of 160±2.0% was reduced to 115±2.0%, which is the same as the control, where the leg was injected with phosphate buffered saline (PBS) (P<0.0005). The results are shown in the sole drawing FIGURE.

To determine the lethal dosage of the venom ($LD_{50}$), different doses of crude venom were prepared in physiological saline and were each injected into four mice (2 mL/dose, 0.5 mL/mouse). The doses were chosen so that no mouse would die at the lower dose, and all mice would die at the higher dose. Mouse mortality within 24 hours was recorded, and each sample $LD_{50}$ was calculated. Upon recordation of mortality, the Spearman-Karber statistical method was used for $LD_{50}$ calculation.

Oral administration of the Ajwa date extract after one hour of lethal dose of venom injection was studied using New Zealand White rabbits. Forty young adult New Zealand White rabbits (6 to 7 months old) of both genders (2.8-3.6 kg) were divided into two groups. Group 1 was divided into five equal subgroups of four rabbits and was injected intraperitoneally (i.p.) with a lethal dose ($LD_{100}$) of *E.c. sochureki* (305 μg/g), *Echis ocellatus* (377 μg/g), *Bitis arietans* (597 μg/g), *Echis pyramidum leakeyi* (500 μg/g) or *Naja n. nigricollis* (155 μg/g) venom alone. Group 2 was divided into five equal subgroups (Groups 2.1 to 2.5) of four rabbits each. All of the subgroups were injected i.p. with the same dose of each venom given above one hour after the Ajwa date extract was administered orally by gastric intubation at a dosage of 1.5 g four times in the first day and twice a day for the subsequent two days. Live and dead animals were examined. An identical procedure was carried out, except with WKY rats and with the Ajwa date extract being administered intravenously (0.5 g/kg per injection).

The results for oral administration are shown below in Table 1. As can be seen, there was no significant difference between the time of death in both the treated and control groups. Although all rabbits treated with the Ajwa date extract died, the time of death was significantly (P<0.05) increased from 0.95 hours to 5.57 hours, in comparison with the control. With regard to the intravenous administration, the results are shown below in Table 2. As can be seen, after one hour of the intravenous administration of the Ajwa date extract, all animals survived. There was no significant difference between the time of death in both the treated and control groups.

TABLE 1

Administration of Ajwa Date Extract Orally After One Hour of Lethal Venom Dose

| | E. c. sochureki (305 μg/g) | Echis ocellatus (377 μg/g) | Bitis arietans (597 μg/g) | Echis pyramidum leakeyi (500 μg/g) | Naja n. nigricolhs (155 μg/g) |
|---|---|---|---|---|---|
| Venom Alone | All died (n = 4) | All died (n = 4) | All died (n = 4) | All died (n = 4) | All died (n = 4) |
| Ajwa Date Extract Via Oral Administration | All died (n = 4) | All died (n = 4) | All died (n = 4) | All died (n = 4) | All died (n = 4) |

TABLE 2

Administration of Ajwa Date Extract Intravenously After One Hour of Lethal Venom Dose

| | E. c. sochureki (305 μg/g) | Echis ocellatus (377 μg/g) | Bitis arietans (597 μg/g) | Echis pyramidum leakeyi (500 μg/g) | Naja n. nigricolhs (155 μg/g) |
|---|---|---|---|---|---|
| Venom Alone | All died (n = 4) | All died (n = 4) | All died (n = 4) | All died (n = 4) | All died (n = 4) |
| Ajwa Date Extract Via Intravenous Administration | All died (n = 4) | All died (n = 4) | All died (n = 4) | All died (n = 4) | All died (n = 4) |

In order to test the effect and safety issues of the Ajwa date extract on healthy mammals, WKY rats received the Ajwa date-based treatment administered at variable dosages to reach an optimum of 16 g/kg for each animal group. The concentration of each fluid dosage containing the herbal composition was about 1 g/mL. Since not every envenomation results in death to the animal, the WKY rats were exposed to double strike with snakebites of both *E. ocellatus* and *B. arietans*. Six WKY rats were exposed to life strike with snake venom after the Ajwa date extract was injected intravenously three times (0.5 g/kg) in the first day and twice in the subsequent day. Another six WKY rats were used as controls. The animals were monitored hourly over the first 24 hours by physical examination. After one hour, four WKY rats of the control group died. The remaining two showed bleeding, necrosis and edema from the site of the snakebite. After 8 hours, the remaining animals in the control group died. In contrast, all WKY rats (n=6), which received the Ajwa date extract by intravenous injection, survived with no sign of clinical complications. The animals were observed with continuous injection (iv) in the subsequent day.

It is to be understood that the present invention is not limited to the embodiments described above, but encompasses any and all embodiments within the scope of the following claims.

We claim:
1. A method of making an Ajwa date-based treatment for snake envenomation, comprising the steps of:
   drying fruit from an Ajwa date palm (*Phoenix dactylifera* L.);
   grinding the dried fruit of the Ajwa date palm;
   mixing the ground and dried fruit with 96% ethanol to form an Ajwa date suspension;

filtering the Ajwa suspension to obtain a filtrate and a non-filtrate solid residue and discarding the non-filtrate solid residue;
drying the filtrate at a temperature of 45° C. to yield a crude extract;
suspending the crude extract in 96% ethanol to form an extraction system;
heating the extraction system at 75° C. overnight;
cooling the heated extraction system over ice to form solids within the extraction system;
filtering the solids from the extraction system after cooling to obtain a second filtrate and discarding the solids; and
lyophilizing the second filtrate to yield a granulated Ajwa date-based treatment for snake envenomation.

2. The method of making an Ajwa date-based treatment for snake envenomation as recited in claim 1, further comprising the step of suspending the granulated Ajwa date-based treatment for snake envenomation in a saline solution.

* * * * *